(12) United States Patent
Simpson et al.

(10) Patent No.: US 8,222,013 B2
(45) Date of Patent: Jul. 17, 2012

(54) BACTERIA AND METHODS OF USE THEREOF

(75) Inventors: Sean Dennis Simpson, Auckland (NZ); Richard Llewellyn Sydney Forster, Pukekohe (NZ); Phuong Loan Tran, Auckland (NZ); Matthew James Rowe, Auckland (NZ); Ian Linstrand Warner, Auckland (NZ)

(73) Assignee: LanzaTech New Zealand Limited, Auckland (NZ)

( * ) Notice: Subject to any disclaimer, the term of this patent is extended or adjusted under 35 U.S.C. 154(b) by 0 days.

(21) Appl. No.: 12/742,149

(22) PCT Filed: Nov. 13, 2008

(86) PCT No.: PCT/NZ2008/000305
§ 371 (c)(1), (2), (4) Date: Aug. 5, 2010

(87) PCT Pub. No.: WO2009/064200
PCT Pub. Date: May 22, 2009

(65) Prior Publication Data
US 2010/0311104 A1    Dec. 9, 2010

Related U.S. Application Data

(60) Provisional application No. 60/987,755, filed on Nov. 13, 2007.

(51) Int. Cl.
*C12P 7/06* (2006.01)
*C12P 7/08* (2006.01)
*C12Q 1/02* (2006.01)
*C12N 1/30* (2006.01)
*C12N 1/28* (2006.01)
*C12N 1/20* (2006.01)

(52) U.S. Cl. ..... 435/161; 435/29; 435/252.1; 435/252.7

(58) Field of Classification Search ..... 435/29, 435/161, 252.1, 252.7
See application file for complete search history.

(56) References Cited

U.S. PATENT DOCUMENTS

| | | | |
|---|---|---|---|
| 5,173,429 A | 12/1992 | Gaddy et al. | |
| 5,593,886 A | 1/1997 | Gaddy | |
| 5,807,722 A | 9/1998 | Gaddy | |
| 5,821,111 A | 10/1998 | Gaddy et al. | |
| 6,136,577 A | 10/2000 | Gaddy | |
| 6,340,581 B1 | 1/2002 | Gaddy | |
| 6,368,819 B1 | 4/2002 | Gaddy et al. | |
| 6,753,170 B2 | 6/2004 | Gaddy et al. | |
| RE39,175 E | 7/2006 | Gaddy et al. | |
| 7,196,218 B2 | 3/2007 | Gaddy et al. | |
| 7,285,402 B2 | 10/2007 | Gaddy et al. | |
| 2006/0051848 A1 | 3/2006 | Nishio et al. | |
| 2007/0275447 A1 | 11/2007 | Lewis et al. | |

FOREIGN PATENT DOCUMENTS

| | | |
|---|---|---|
| EP | 1550714 | 7/2005 |
| WO | 2008/028055 | 3/2008 |
| WO | 2008/115080 | 9/2008 |
| WO | 2008/154301 | 12/2008 |
| WO | 2009/020747 | 2/2009 |

OTHER PUBLICATIONS

Rajagopalan et al., 2002. Formation of ethanol from carbon monoxide via a new microbial catalyst. Biomass and Bioenergy, vol. 23, pp. 487-493.*
Tibbles et al 1992. Estimates of Bacterial Productivity in Marine Sediments and Water from a Temperate Saltmarsh Lagoon. Microbial Ecology, vol. 23, pp. 195-209.*
Dragone et al. 2003. Improvement of the ethanol productivity in a high gravity brewing at pilot plant scale. Biotechnology Letters, vol. 25, pp. 1171-1174.*
Younesi H. et al. "Liquid fuel production from synthesis gas via fermentation process in a continuous tank bioreactor (CSTBR) using *Clostridium ljungdahlii*". Iranian Journal of Biotechnology. 2006, vol. 4, No. 1, pp. 45-53.
Datar, R.P. et al. "Fermentation of Biomass-Generated Producer Gas to Ethanol". Biotechnology and Bioengineering, 2004, vol. 86, No. 5 pp. 587-594.
Abrini, J. et al. "*Clostridium autoethanogenum*, sp. Nov., an anaerobic bacterium that produces ethanol from carbon monoxide". Archives from Microbiology. 1994, vol. 161, No. 4, pp. 345-351.
Ragsdale, Stephen. "Life with Carbon Monoxide." 2004. Critical Reviews in Biochemistry and Molecular Biology, pp. 165-195.
Phillips et al. "Synthesis gas as substrate for the biological production of fuels and chemicals", 1994. Applied Biochemistry and Biotechnology, 45(1), pp. 145-157.
Henstra, Anne M et al. "Microbiology of synthesis gas fermentation for biofuel production." 2007. ScienceDirect (www.sciencedirect.com) pp. 200-206.
Najafpour, Ghasem, et al. "Ethanol and acetate synthesis from waste gas using batch culture of *Clostridium ljungdahlii*" *Enzyme and Microbial Technology*, vol. 38, No. 1-2 (Jan. 3, 2006) pp. 223-228.
Rainey, et al. "Phylogenetic Analysis of Anaerobic Thermophilic Bacteria: Aid for their Reclassification" *Journal of Bacteriology*, American Society for Microbiology, vol. 175, No. 15, (Aug. 1, 1993) pp. 4772-4779.

* cited by examiner

*Primary Examiner* — Jon P Weber
*Assistant Examiner* — Kailash C Srivastava
(74) *Attorney, Agent, or Firm* — Frank S Molinaro

(57) ABSTRACT

A novel class of bacteria is described which has improved efficiency in the production of thanol by anaerobic fermentation of substrates containing carbon monoxide.

7 Claims, 1 Drawing Sheet

BACTERIA AND METHODS OF USE THEREOF

CROSS REFERENCE TO RELATED APPLICATIONS

This application is a National Stage of International Application No. PCT/NZ2008/000305, filed on Nov. 13, 2008, which claims priority to U.S. Provisional Application 60/987,755 filed Nov. 13, 2007. The contents of the prior applications mentioned above are incorporated herein by reference.

FIELD OF THE INVENTION

This invention relates generally to the field of microbial fermentation of gases. It more particularly relates to a novel class of bacteria with improved efficiency in the production of ethanol by anaerobic fermentation of substrates containing carbon monoxide (CO).

BACKGROUND OF THE INVENTION

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to grow sharply in future, due to an increased interest in ethanol in Europe, Japan, the USA, and several developing nations.

For example, in the USA, ethanol is used to produce E10, a 10% mixture of ethanol in gasoline. In E10 blends the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, while the cultivation of starch or sucrose-producing crops for ethanol production is not economically sustainable in all geographies. Therefore, it is of interest to develop technologies to convert lower cost and/or more abundant carbon resources into fuel ethanol.

CO is a major, free, energy-rich by-product of the incomplete combustion of organic materials such as coal or oil and oil derived products. For example, the steel industry in Australia is reported to produce and release into the atmosphere over 500,000 tonnes of CO annually.

Catalytic processes may be used to convert gases consisting primarily of CO and/or CO and hydrogen (H2) into a variety of fuels and chemicals. Micro-organisms may also be used to convert these gases into fuels and chemicals.

The ability of micro-organisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely CO2, H2, methane, n-butanol, acetate and ethanol. While using CO as the sole carbon source, all such organisms produce at least two of these end products.

Anaerobic bacteria, such as those from the genus *Clostridium*, have been demonstrated to produce ethanol from CO, CO2 and H2 via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al., Archives of Microbiology 161, pp 345-351 (1994)).

However, ethanol production by micro-organisms by fermentation of gases is always associated with co-production of acetate and/or acetic acid. As some of the available carbon is converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to GHG emissions.

Microbial fermentation of CO in the presence of H2 can lead to substantially complete carbon transfer into an alcohol. However, in the absence of sufficient H2, some of the CO is converted into alcohol, while a significant portion is converted to CO2 as shown in the following equations:

$$6CO + 3H_2O \rightarrow C_2H_5OH + 4CO_2$$

$$12H_2 + 4CO_2 \rightarrow 2C_2H_5OH + 6H_2O$$

The production of $CO_2$ represents inefficiency in overall carbon capture and if released, also has the potential to contribute to Green House Gas emissions.

WO2007/117157 describes a process that produces alcohols, particularly ethanol, by anaerobic fermentation of gases containing carbon monoxide. Acetate produced as a by-product of the fermentation process is converted into hydrogen gas and carbon dioxide gas, either or both of which may be used in the anaerobic fermentation process.

WO2008/115080 describes a process for the production of alcohol(s) in multiple fermentation stages. By-products produced as a result of anaerobic fermentation of gas(es) in a first bioreactor can be used to produce products in a second bioreactor. Furthermore, by-products of the second fermentation stage can be recycled to the first bioreactor to produce products.

It would thus be beneficial to provide micro-organisms that are capable of fermentation of such gases to ethanol at increased efficiency, that is micro-organisms capable of producing more ethanol, and/or a greater ratio of ethanol to acetate from the same substrate, than do micro-organisms of the prior art.

In addition, in prior art methods of bacterial fermentation of CO-containing gases to ethanol that produce high levels of ethanol and/or a high ethanol to acetate ratio, the gaseous substrate used typically comprises about 30-65% CO by volume and about 20-30% $H_2$ by volume (WO 00/68407).

CO-containing waste gases, that are potential substrates for microbial fermentation to produce ethanol, may contain either higher levels of CO and lower levels of $H_2$ or both. It would therefore be beneficial to have available bacterial strains that can perform efficient fermentation of CO-containing gas with greater than 65% CO by volume and or less than 20% $H_2$ by volume into ethanol, for example.

It is an object of the present invention to provide a new class of bacteria which overcomes one or more of the limitations of the prior art in the conversion of gaseous sources containing CO into ethanol, or at least to provide the public with a useful choice.

SUMMARY OF THE INVENTION

In a first aspect the invention provides a biologically pure isolate of a bacterium capable of producing products including ethanol and optionally acetate, by anaerobic fermentation of a substrate comprising CO, wherein the products are produced at an ethanol to acetate ratio of at least 1.0.

In another aspect the invention provides a biologically pure isolate of a bacterium capable of producing ethanol and acetate by anaerobic fermentation in an aqueous culture medium supplied with a substrate containing CO, particularly a gaseous substrate containing CO, comprising:

(a) greater than about 65% CO by volume
(b) less than about 20% $H_2$ by volume, or
(c) greater than about 65% CO and less than about 20% $H_2$ by volume, at an ethanol to acetate ratio of at least about 1.0.

In one particular embodiment the ethanol to acetate ratio is at least about 1.1, more preferably at least about 1.2, more preferably at least about 1.3 and most preferably at least about 1.4.

In a further embodiment the bacterium is capable of producing the ethanol at a concentration of at least about 2.0 g ethanol per litre of fermentation broth.

In particular embodiments the concentration is at least about 2.1 g ethanol per litre of fermentation broth, at least about 2.2 g ethanol per litre of fermentation broth, at least about 2.3 g ethanol per litre of fermentation broth, at least about 2.4 g ethanol per litre of fermentation broth, at least about 2.5 g ethanol per litre of fermentation broth, at least about 2.6 g ethanol per litre of fermentation broth, at least about 2.7 g ethanol per litre of fermentation broth at least about 2.8 g ethanol per litre of fermentation broth, at least about 3.0 g ethanol per litre of fermentation broth, at least about 3.2 g ethanol per litre of fermentation broth, or at least about 3.4 g ethanol per litre of fermentation broth.

In particular embodiments the productivity of the bacterium is at least about 1.2 g of ethanol/L of fermentation broth/day, at least about 1.6 g/L/day, at least about 1.8 g/L/day or at least 2.0 g/L/day.

In certain embodiments, the specific ethanol productivity of the bacterium is at least about 0.7 g/L/gram bacterial cells/day, at least about 0.9 g/L/gram bacterial cells/day, at least about 1.1 g/L/gram bacterial cells/day, or at least about 1.3 g/L/gram bacterial cells/day.

In another aspect the invention provides a biologically pure isolate of a bacterium capable of producing products including alcohol and optionally acetate, by anaerobic fermentation of a substrate comprising CO, wherein the productivity of the bacterium is at least about 1.2 g of ethanol/L of fermentation broth/day.

In a further aspect the invention provides a biologically pure isolate of a bacterium capable of producing ethanol by anaerobic fermentation in an aqueous culture medium supplied with a substrate containing CO, particularly a gaseous substrate containing CO, comprising:

(a) greater than about 65% CO by volume
(b) less than about 20% $H_2$ by volume, or
(c) greater than about 65% CO and less than about 20% $H_2$ by volume, at an ethanol concentration of at least about 2.0 g ethanol per litre of fermentation broth.

In particular embodiments the concentration is at least about 2.1 g ethanol per litre of fermentation broth, at least about 2.2 g ethanol per litre of fermentation broth, at least about 2.3 g ethanol per litre of fermentation broth, at least about 2.4 g ethanol per litre of fermentation broth, at least about 2.5 g ethanol per litre of fermentation broth, at least about 2.6 g ethanol per litre of fermentation broth, at least about 2.7 g ethanol per litre of fermentation broth at least about 2.8 g ethanol per litre of fermentation broth, at least about 3.0 g ethanol per litre of fermentation broth, at least about 3.2 g ethanol per litre of fermentation broth, or at least about 3.4 g ethanol per litre of fermentation broth.

In particular embodiments the productivity of the bacterium is at least about 1.2 g of ethanol/L of fermentation broth/day, at least about 1.6 g/L/day, at least about 1.8 g/L/day or at least 2.0 g/L/day.

In certain embodiments, the specific ethanol productivity of the bacterium is at least about 0.7 g/L/gram bacterial cells/day, at least about 0.9 g/L/gram bacterial cells/day, at least about 1.1 g/L/gram bacterial cells/day, or at least about 1.3 g/L/gram bacterial cells/day.

In one embodiment acetate is produced as a by-product of the fermentation.

In a particular embodiment the ethanol is produced at an ethanol to acetate ratio of at least about 1.0. In particular embodiments the ethanol to acetate ratio is at least about 1.1, at least about 1.2, at least about 1.3 or more particularly at least about 1.4.

In another aspect, the invention provides an acetogenic bacterium wherein the bacterium has one or more of the following defining characteristics:

an ability to grow in minimal medium in the presence or absence of yeast extract;
an ability to grow more rapidly, to produce a higher ratio of ethanol to acetate, and/or to produce a higher concentration of ethanol, in a medium in which yeast extract is not present compared to a medium in which yeast extract is present;
little or no ability to sporulate;
Gram positive;
rod shaped;
Non-motile.

In one embodiment the bacteria are additionally capable of producing ethanol by anaerobic fermentation in an aqueous culture medium supplied with a CO-containing substrate comprising:

(a) greater than about 65% CO by volume,
(b) less than about 20% $H_2$ by volume, or
(c) greater than about 65% CO and less than about 20% $H_2$ by volume, at an ethanol concentration of at least about 2.0 g ethanol per litre of fermentation broth and/or at an ethanol to acetate ratio of at least about 1.0.

In particular embodiments the ethanol to acetate ratio is at least about 1.1, at least about 1.2, at least about 1.3 or more particularly at least about 1.4.

In particular embodiments the concentration of ethanol produced is at least about 2.1 g ethanol per litre of fermentation broth, at least about 2.2 g ethanol per litre of fermentation broth, at least about 2.3 g ethanol per litre of fermentation broth, at least about 2.4 g ethanol per litre of fermentation broth, at least about 2.5 g ethanol per litre of fermentation broth, at least about 2.6 g ethanol per litre of fermentation broth, at least about 2.7 g ethanol per litre of fermentation broth at least about 2.8 g ethanol per litre of fermentation broth, at least about 3.0 g ethanol per litre of fermentation broth, at least about 3.2 g ethanol per litre of fermentation broth, or at least about 3.4 g ethanol per litre of fermentation broth.

In particular embodiments the productivity of the bacterium is at least about 1.2 g of ethanol/L of fermentation broth/day, at least about 1.6 g/L/day, at least about 1.8 g/L/day or at least 2.0 g/L/day.

In certain embodiments, the specific ethanol productivity of the bacterium is at least about 0.7 g/L/gram bacterial cells/day, at least about 0.9 g/L/gram bacterial cells/day, at least about 1.1 g/L/gram bacterial cells/day, or at least about 1.3 g/L/gram bacterial cells/day.

In one embodiment, the bacteria of the invention are derived from *Clostridium autoethanogenum*.

In a particular embodiment, the bacteria have two or more and most preferably all of the above defining characteristics.

In a particular embodiment the bacterium has the defining characteristics of *Clostridium autoethanogenum* strain LBS1560 deposited at DSMZ under the accession number DSM 19630. In one embodiment the bacterium is *Clostridium autoethanogenum* strain LBS1560 deposited at DSMZ under the accession number DSM 19630.

In a further aspect the invention provides a biologically pure isolate of *Clostridium autoethanogenum* strain LBS1560 deposited at DSMZ under the accession number. DSM 19630.

In one embodiment the substrate comprises at least about 70% CO by volume, at least about 75% CO by volume, at least about 80% CO by volume, at least about 85% CO by volume, at least about 90% CO by volume or at least about 95% CO by volume.

In a further embodiment the substrate comprises less than about 20% $H_2$ by volume. In particular embodiments the substrate comprises less than about 15% $H_2$ by volume, less than about 10% $H_2$ by volume, less than about 5% $H_2$ by volume, less than about 4% $H_2$ by volume, less than about 3% $H_2$ by volume, less than about 2% $H_2$ by volume, less than about 1% $H_2$ by volume, or substantially no $H_2$.

In a further embodiment the substrate comprises less than or equal to about 20% $CO_2$ by volume. In particular embodiments the substrate comprises less than or equal to about 15% $CO_2$ by volume, less than or equal to about 10% $CO_2$ by volume, or less than or equal to about 5% $CO_2$ by volume.

In particular embodiments the substrate comprises at least about 85% CO by volume and at most about 15% $CO_2$ by volume, at least about 90% CO and at most about 10% $CO_2$, or about 95% CO by volume and about 5% $CO_2$ by volume.

In certain embodiments the aqueous culture medium is a minimal anaerobic microbial growth medium selected from but not limited to LM23 or LM33 as herein defined.

In one embodiment, the medium is not supplemented with yeast extract.

In a further aspect, the invention provides a method for the production of one or more alcohols from a substrate containing CO, the method comprising maintaining a culture of one or more of the bacterial isolates of the invention in the presence of the substrate, and the anaerobic fermentation of the substrate to one or more alcohols by the one or more bacterial isolate.

In another aspect, the invention provides a method for the production of one or more alcohols comprising fermenting a substrate containing CO using one or more of the bacteria as herein before described.

In one embodiment the method comprises the steps of:
(a) providing a substrate containing CO to a bioreactor containing a culture of a bacterium as hereinbefore described; and
(b) anaerobically fermenting the culture in the bioreactor to produce one or more alcohols.

In a further aspect, the invention provides a method for reducing the total atmospheric carbon emissions from an industrial process, the method comprising:
(a) capturing CO-containing gas produced as a result of the industrial process, before the gas is released into the atmosphere;
(b) the anaerobic fermentation of the CO-containing gas to produce one or more alcohols by a culture containing one or more bacterial isolates of the invention.

In certain embodiments of the method aspects, acetate is produced as a by-product of the fermentation. Preferably the one or more alcohols produced includes ethanol.

In particular embodiments of the method aspects, the bacterium or isolate is maintained in an aqueous culture medium.

In particular embodiments of the method aspects, the fermentation of the substrate takes place in a bioreactor.

In certain embodiments, the substrate contains less than about 15% $H_2$ by volume, such as less than about 10% $H_2$, such as less than about 5% $H_2$.

In certain embodiments, the substrate comprises greater than about 65% CO by volume, preferably about 70% CO to about 95% CO by volume.

In one embodiment the substrate comprises at least about 70% CO by volume. In a particular embodiment the substrate comprises at least about 80% CO by volume, at least about 85% CO by volume, at least about 90% CO by volume or at least about 95% CO by volume.

In one embodiment the substrate comprises less than about 20% $H_2$ by volume. In particular embodiments the substrate comprises less than about 15% $H_2$ by volume, less than about 10% $H_2$ by volume, less than about 5% $H_2$ by volume, less than about 4% $H_2$ by volume, less than about 3% $H_2$ by volume, less than about 2% $H_2$ by volume, less than about 1% $H_2$ by volume, or substantially no $H_2$.

In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, or less than or equal to about 5% $CO_2$ by volume.

In certain embodiments the substrate comprises at least about 85% CO by volume and at most about 15% $CO_2$ by volume, at least about 90% CO and at most about 10% CO2, or about 95% CO by volume and about 5% $CO_2$ by volume.

In certain embodiments the substrate containing CO is a gaseous substrate containing CO.

In certain embodiments, the gaseous substrate comprises a gas obtained as a by-product of an industrial process.

In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing.

In one embodiment, the gaseous substrate may comprise a gas obtained from a steel mill.

In another embodiment, the gaseous substrate may comprise automobile exhaust fumes.

In certain embodiments of the method aspects the alcohol is recovered from the fermentation broth, the fermentation broth being the aqueous culture medium comprising bacterial cells and the alcohol.

In certain embodiments acetate is produced as a by-product of the fermentation.

In a further embodiment the alcohol and the acetate are recovered from the broth.

In another aspect, the invention provides a method of selection of one or more micro-organisms which produce one or more acids, the method comprising: Culturing the micro-organisms in a nutrient media in a bioreactor; Adding fresh media at a pH higher than the nutrient media, such that the nutrient media is maintained at a substantially constant pH; and, Removing at least a portion of the nutrient medium and micro-organisms, such that the medium in the bioreactor is maintained at a substantially constant volume.

In a particular embodiment, the method is for the selection of fast growing micro-organisms. In one embodiment the one or more acids includes acetate.

In another aspect the invention provides a biologically pure isolate of a bacterium produced by the method of selection. In one embodiment, the isolate has little or no ability to sporulate.

Although the invention is broadly as defined above, it is not limited thereto and also includes embodiments of which the following description provides examples.

BRIEF DESCRIPTION OF THE DRAWINGS

The invention will now be described in detail with reference to the accompanying Figures in which.

DETAILED DESCRIPTION OF THE INVENTION

In broad terms, in one aspect the present invention relates to a novel bacterium and a biologically pure isolate of a bacterium with increased efficiency in an anaerobic fermentation process. In one aspect the bacterium is capable of producing an alcohol, preferably ethanol, from a substrate comprising:

(a) greater than about 65% CO by volume
(b) less than about 20% $H_2$ by volume, or
(c) greater than about 65% CO and less than about 20% $H_2$ by volume.

In a further aspect, the invention relates to a process for producing an alcohol, preferably ethanol, by anaerobic fermentation of a CO-containing substrate by the bacteria of the invention.

DEFINITIONS

Unless otherwise defined, the following terms as used throughout this specification are defined as follows:

A "substrate containing CO" and like terms should be understood to include any substrate in which carbon monoxide is available to bacteria for growth and/or fermentation, for example. In particular embodiments of the invention the "substrate containing CO" is gaseous. Such substrates may be referred to herein as "gaseous substrates containing CO" and the like.

In the description which follows, embodiments of the invention are described in terms of delivering and fermenting a "gaseous substrate containing CO". However, it should be appreciated that the gaseous substrate may be provided in alternative forms. For example, the gaseous substrate containing CO may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October, 2002) could be used. By way of further example, the gaseous substrate containing CO may be adsorbed onto a solid support. Such alternative methods are encompassed by use of the term "substrate containing CO".

The terms "increasing the efficiency", "increased efficiency" and the like, when used in relation to a fermentation process, include, but are not limited to, increasing one or more of: the rate of growth of micro-organisms catalysing the fermentation, the volume of desired product (such as alcohols) produced per volume of substrate (such as CO) consumed, the concentration of the desired product (such as alcohols) produced in the culture medium, the rate of production or level of production of the desired product, and the relative proportion of the desired product produced compared with other by-products of the fermentation.

The term "acetate" includes both acetate salt alone and a mixture of molecular or free acetic acid and acetate salt, such as the mixture of acetate salt and free acetic acid present in a fermentation broth as described herein. The ratio of molecular acetic acid to acetate in the fermentation broth is dependent upon the pH of the system.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact.

Bacteria of the invention, or cultures or isolates thereof, may be described to be in an "isolated" or "biologically pure" form. These terms are intended to mean that the bacteria have been separated from an environment or one or more constituents, cellular or otherwise, which they may be associated with if found in nature or otherwise. The terms "isolated" or "biologically pure" should not be taken to indicate the extent to which the bacteria have been purified. However, in one embodiment the isolates or cultures of the bacteria contain a predominance of the bacteria of the invention.

The invention provides a biologically pure isolate of a bacterium capable of producing ethanol and acetate by anaerobic fermentation in an aqueous culture medium supplied with a gaseous CO-containing substrate comprising:

(a) greater than about 65% CO by volume
(b) less than about 20% $H_2$ by volume, or
(c) greater than about 65% CO and less than about 20% $H_2$ by volume, at an ethanol to acetate ratio of at least about 1.0. In one embodiment, the bacterium is derived from C. autoethanogenum as described elsewhere herein.

In certain embodiments the ethanol to acetate ratio is at least about 1.1, or at least about 1.2, or at least about 1.3 or at least about 1.4.

In further embodiments the bacterium is capable of producing ethanol at a concentration of at least about 2.1 g ethanol per litre of fermentation broth, at least about 2.2 g ethanol per litre of fermentation broth, at least about 2.3 g ethanol per litre of fermentation broth, at least about 2.4 g ethanol per litre of fermentation broth, at least about 2.5 g ethanol per litre of fermentation broth, at least about 2.6 g ethanol per litre of fermentation broth, at least about 2.7 g ethanol per litre of fermentation broth at least about 2.8 g ethanol per litre of fermentation broth, at least about 3.0 g ethanol per litre of fermentation broth, at least about 3.2 g ethanol per litre of fermentation broth, or at least about 3.4 g ethanol per litre of fermentation broth.

Ethanol productivity is the volumetric productivity of ethanol, calculated as the ratio of the ethanol concentration and the time required to produce that concentration in batch systems. Productivity can also be calculated for microbial fermentation in continuous systems. In particular embodiments of the invention, the productivity of the bacteria is at least 1.2 g ethanol/L of fermentation broth/day, or at least 1.6 g/L/day or at least 1.8 g/L/day or at least 2.0 g/L/day.

The specific productivity of a microbial culture depends on the proportion of live active microorganism within a microbial culture. In certain embodiments of the present invention, the specific ethanol productivity is at least 0.7 g/L/gram bacterial cells/day, or at least 0.9 g/L/gram bacterial cells/day, or at least 1.1 g/L/gram bacterial cells/day, or at least 1.3 g/L/gram bacterial cells/day.

The invention also provides a biologically pure isolate of a bacterium capable of producing ethanol by anaerobic fermentation in an aqueous culture medium supplied with a gaseous CO-containing substrate comprising:

(a) greater than about 65% CO by volume
(b) less than about 20% $H_2$ by volume, or
(c) greater than about 65% CO and less than about 20% $H_2$ by volume, at an ethanol concentration of at least 2.0 g ethanol per litre of fermentation broth. In one embodiment, the bacterium is derived from *C. autoethanogenum* as described elsewhere herein.

In further embodiments the bacterium is capable of producing ethanol at a concentration of at least about 2.1 g ethanol per litre of fermentation broth, at least about 2.2 g ethanol per litre of fermentation broth, at least about 2.3 g ethanol per litre of fermentation broth, at least about 2.4 g ethanol per litre of fermentation broth, at least about 2.5 g ethanol per litre of fermentation broth, at least about 2.6 g ethanol per litre of fermentation broth, at least about 2.7 g ethanol per litre of fermentation broth at least about 2.8 g ethanol per litre of fermentation broth, at least about 3.0 g ethanol per litre of fermentation broth, at least about 3.2 g ethanol per litre of fermentation broth, or at least about 3.4 g ethanol per litre of fermentation broth.

In particular embodiments of the invention, the productivity of the bacteria is at least 1.2 g ethanol/L of fermentation broth/day, or at least 1.6 g/L/day or at least 1.8 g/L/day or at least 2.0 g/L/day.

In certain embodiments of the present invention, the specific ethanol productivity is at least 0.7 g/L/gram bacterial cells/day, or at least 0.9 g/L/gram bacterial cells/day, or at least 1.1 g/L/gram bacterial cells/day, or at least 1.3 g/L/gram bacterial cells/day.

Typically acetate is produced as a by-product of the fermentation. In one embodiment the ethanol is produced at an ethanol to acetate ratio of at least about 1.0. In particular embodiments the ethanol to acetate ratio is at least about 1.1, or at least about 1.2, or at least about 1.3 or at least about 1.4.

The invention also provides acetogenic bacteria having one or more of the following defining characteristics as observed under the experimental conditions described herein after: an ability to grow in minimal medium in the presence or absence of yeast extract; an ability to grow more rapidly, to produce a higher ratio of ethanol to acetate, and/or to produce a higher concentration of ethanol, in a medium in which yeast extract is not present compared to a medium in which yeast extract is present; little or no ability to sporulate; Gram positive; rod shaped; Non-motile.

In one embodiment the bacteria have substantially no ability to sporulate. In one embodiment substantially none of the bacterial population exhibit spores under the conditions described herein after.

In one embodiment the acetogenic bacteria are additionally capable of producing ethanol by anaerobic fermentation in an aqueous culture medium supplied with a CO-containing substrate comprising: greater than about 65% CO by volume; less than about 20% $H_2$ by volume; or, greater than about 65% CO and less than about 20% $H_2$ by volume; at an ethanol concentration of at least about 2.0 g ethanol per litre of fermentation broth and/or at an ethanol to acetate ratio of at least about 1.0.

The bacteria of the invention can be derived from *Clostridium autoethanogenum*.

The observation that bacteria of certain embodiments of the invention have little to no ability to sporulate is surprising. This provides an unexpected benefit over other strains of *Clostridia* including *Clostridium autoethanogenum*. Sporulation is a stagnant phase of limited activity. Reducing or ameliorating the ability to form spores has a number of advantages. For example, a single bacterial cell can only divide and produce metabolites (such as acetate and/or ethanol) while in a non sporulated condition. Accordingly, the time scale for division and metabolite production can be extended where bacteria do not sporulate. The lack of an ability to sporulate may also provide additional control over an entire culture, wherein the whole live population may be adapted to promote growth and/or metabolite production for extended periods. Therefore, use of bacteria of the present invention may increase the overall efficiency of a fermentation process for producing products such as acetate and/or ethanol.

In certain embodiments of the invention, the bacteria have two or more and more preferably all of the above mentioned characteristics. In some embodiments of the invention the bacteria have the defining characteristics of *Clostridium autoethanogenum* strain LBS1560 deposited at DSMZ, Germany, in accordance with the Budapest Treaty, on 19 Oct. 2007, and allocated the accession number DSM 19630. In a particular embodiment, the bacterium is *Clostridium autoethanogenum* strain LBS1560, DSM 19630.

The invention also relates to bacteria derived from the bacteria of the invention.

In certain embodiments the bacteria of the invention are able to produce the concentrations of ethanol, and ethanol to acetate ratios discussed above, at elevated levels of CO in the gaseous substrate. The gaseous substrate may comprise at least about 70% CO by volume. In certain embodiments the gaseous substrate comprises at least about 80% CO by volume, or at least about 85% CO by volume, or at least about 90% CO by volume or at least about 95% CO by volume.

Similarly the discussed ethanol concentrations, and ethanol to acetate ratios, are achievable in certain embodiments at low to non-existent levels of $H_2$ in the gaseous substrate. The gaseous substrate may comprise less than about 20% $H_2$ by volume. In particular embodiments the gaseous substrate comprises less than about 15% $H_2$ by volume, or the gaseous substrate comprises less than about 10% $H_2$ by volume, or the gaseous substrate comprises less than about 5% $H_2$ by volume, or the gaseous substrate comprises less than about 4% $H_2$ by volume, or the gaseous substrate comprises less than about 3% $H_2$ by volume, or the gaseous substrate comprises less than about 2% $H_2$ by volume, or the gaseous substrate comprises less than about 1% $H_2$ by volume, or the gaseous substrate comprises no $H_2$.

In certain embodiments, the bacteria of the invention can also produce ethanol concentrations, and ethanol to acetate ratios when supplied with gaseous substrate comprising relatively little $CO_2$. In one embodiment the gaseous substrate comprises less than or equal to about 20% $CO_2$ by volume. In certain embodiments the gaseous substrate comprises less than or equal to about 15% $CO_2$ by volume, or less than or equal to about 10% $CO_2$ by volume, or less than or equal to about 5% $CO_2$ by volume.

In certain embodiments the gaseous substrate comprises about 85% CO by volume and about 15% $CO_2$ by volume, or the gaseous substrate comprises at least about 90% CO and at most about 10% $CO_2$, or the gaseous substrate comprises about 95% CO by volume and about 5% $CO_2$ by volume.

In certain embodiments the culture is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and in Klasson et al [(1992). Bioconversion of Synthesis Gas into Liquid or Gaseous Fuels. Enz. Microb. Technol. 14:602-608.], Najafpour and Younesi [(2006). Ethanol and acetate synthesis from waste gas using batch culture of *Clostridium ljungdahlii*. Enzyme and Microbial Technology, Volume 38, Issues 1-2, p. 223-228] and Lewis et al [(2002). Making the connection-conversion of biomass-generated producer gas to ethanol. Abst. Bioenergy, p. 2091-2094.]. In particular embodiments of the invention, the minimal anaerobic microbial growth medium is LM23 or LM33 as herein defined.

In certain embodiments the medium is supplemented with additional components, such as but not limited to amino acids and trypticase. Preferably the medium is not supplemented with additional components.

In certain embodiments the medium may be supplemented with yeast extract. In certain embodiments the culture grows more rapidly when the medium is not supplemented with yeast extract, than when the medium is supplemented with yeast extract. In a further embodiment the ethanol to acetate ratio produced is higher when the medium is not supplemented with yeast extract, than when the medium is supplemented with yeast extract. In a further embodiment the concentration of ethanol produced per litre of culture medium is higher when the medium is not supplemented with yeast extract, than when the medium is supplemented with yeast extract. In a particular embodiment, the medium is not supplemented with yeast extract.

The invention also provides methods for the production of one or more alcohols from a gaseous substrate comprising CO, the methods comprising maintaining a culture of one or more bacterial isolate of the invention in the presence of the gaseous substrate, and the anaerobic fermentation of the gaseous substrate to one or more alcohols by the one or more bacterial isolate.

The invention also provides a method for reducing the total atmospheric carbon emissions from an industrial process, the method comprising:

(a) capturing CO-containing gas produced as a result of the industrial process, before the gas is released into the atmosphere;

(b) the anaerobic fermentation of the CO-containing gas to produce one or more alcohols by a culture containing one or more bacterial isolates of the invention.

In certain embodiments of the methods of the invention, acetate is produced as a by-product of the fermentation. The alcohol produced is ethanol.

In certain embodiments, the culture is maintained in a liquid nutrient medium.

The fermentation may be carried out in any suitable bioreactor, such as a continuous stirred tank reactor (CTSR), a bubble column reactor (BCR) or a trickle bed reactor (TBR). Also, in some preferred embodiments of the invention, the bioreactor may comprise a first, growth reactor in which the micro-organisms are cultured, and a second, fermentation reactor, to which fermentation broth from the growth reactor is fed and in which most of the fermentation product (ethanol and acetate) is produced.

As described above, the carbon source for the fermentation reaction is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

In addition, it is often desirable to increase the CO concentration of a substrate stream (or CO partial pressure in a gaseous substrate) and thus increase the efficiency of fermentation reactions where CO is a substrate. Increasing CO partial pressure in a gaseous substrate increases CO mass transfer into a fermentation medium. The composition of gas streams used to feed a fermentation reaction can have a significant impact on the efficiency and/or costs of that reaction. For example, O2 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

Substrate streams derived from an industrial source are typically variable in composition. Furthermore, substrate streams derived from industrial sources comprising high CO concentrations (such as at least 50% CO or at least 65%) often have a low H2 component (such as less than 20% or less than 10% or 0%). As such, it is particularly desirable that microorganisms are capable of producing products by anaerobic fermentation of substrates comprising a range of CO and H2 concentrations, particularly high CO concentrations and low H2 concentrations. The inventors tested *C. autoethanogenum* (obtained from DSMZ under accession number DSM 10061) and note it would not grow and produce products on gaseous substrates comprising CO without an H2 component. However, the bacteria of the present invention have the surprising ability to grow and produce products (ethanol and acetate) by fermenting a substrate comprising CO (and no H2).

The presence of hydrogen in the substrate stream can lead to an improvement in efficiency of overall carbon capture and/or ethanol productivity. For example, WO02/08438 describes the production of ethanol using gas stream of various compositions. WO02/08438 reports a substrate stream comprising 63% H2, 32% CO and 5% CH4 being provided to a culture of *C. ljungdahlii* in a bioreactor to promote microbial growth and ethanol production. When the culture reached a steady state and microbial growth was no longer the main objective, the substrate stream was switched to 15.8% H2, 36.5% CO, 38.4% N2 and 9.3% CO2 in order to provide CO in a slight excess and promote ethanol production. This document also describes gas streams with higher and lower CO and H2 concentrations.

It will be appreciated that the processes of the present invention as described herein can be used to reduce the total atmospheric carbon emissions from industrial processes, by capturing CO-containing gases produced as a result of such processes and using them as substrates for the fermentation processes described herein.

Alternatively, in other embodiments of the invention, the CO-containing gaseous substrate may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

It is generally preferred that the CO-containing gaseous substrate contains a major proportion of CO. In particular embodiments, the gaseous substrate comprises at least about 65%, or at least about 70% to about 95% CO by volume. It is not necessary for the gaseous substrate to contain any hydrogen. The gaseous substrate also optionally contains some $CO_2$, such as about 1% to about 30% by volume, such as about 5% to about 10% $CO_2$.

It will be appreciated that for growth of the bacteria and CO-to-ethanol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438 as well as other publications referred to herein before. In one embodiment of the invention the medium is LM23 as described in the Examples herein after.

The fermentation should desirably be carried out under appropriate conditions for the CO-to-ethanol fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

The optimum reaction conditions will depend partly on the particular micro-organism of the invention used. However, in general, it is preferred that the fermentation be performed at pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, since a given CO-to-ethanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per litre per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

In certain embodiments, a fermentation process according to the present invention described above will result in a fermentation broth comprising ethanol, as well as bacterial cells, in the aqueous culture medium. In preferred embodiments of the method the ethanol is recovered from the fermentation broth.

In certain embodiments, the recovering of ethanol comprises continuously removing a portion of broth and recovering the alcohol from the removed portion of the broth.

In particular embodiments the recovery of ethanol includes passing the removed portion of the broth containing ethanol through a separation unit to separate bacterial cells from the broth, to produce a cell-free alcohol-containing permeate, and returning the bacterial cells to the bioreactor.

In certain embodiments, the methods of the invention are continuous processes.

In particular embodiments acetate is produced as a by-product of the fermentation.

In a further embodiment the ethanol and the acetate are recovered from the broth.

In certain embodiments, the recovering of ethanol and acetate comprises continuously removing a portion of the broth and recovering separately ethanol and acetate from the removed portion of the broth.

In some embodiments the recovery of ethanol and acetate includes passing the removed portion of the broth containing ethanol and acetate through a separation unit to separate bacterial cells from the ethanol and acetate, to produce a cell-free ethanol-and acetate-containing permeate, and returning the bacterial cells to the bioreactor.

In the above embodiments, the recovery of ethanol and acetate preferably includes first removing ethanol from the cell-free permeate followed by removing acetate from the cell-free permeate. Preferably the cell-free permeate is then returned to the bioreactor.

In certain embodiments, the methods of the invention are continuous processes.

Ethanol is the preferred desired end product of the fermentation. The ethanol may be recovered from the fermentation broth by methods known in the art, such as fractional distillation or evaporation, and extractive fermentation. Distillation of ethanol from a fermentation broth yields an azeotropic mixture of ethanol and water (i.e. 95% ethanol and 5% water). Anhydrous ethanol can subsequently be obtained through the use of molecular sieve ethanol dehydration technology, which is also well known in the art. Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non volatile and is recovered for re-use in the fermentation.

Acetate may also be recovered from the fermentation broth using methods known in the art. Methods for the recovery of acetate are described in detail in WO2007/117157 and WO2008/115080.

In certain embodiments of the invention, ethanol and acetate are recovered from the fermentation broth by continuously removing a portion of the broth from the fermentation bioreactor, separating microbial cells from the broth (conveniently by filtration), and recovering first ethanol and then acetate from the broth. The ethanol may conveniently be recovered by distillation, and the acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Reaction Stoichiometry

Without wishing to be bound by any theory, the chemical reactions for the fermentation of CO to ethanol (a) and acetic acid (b) in the process of the present invention are believed to be as follows:

(a) $18CO + 9H_2O \Rightarrow 3CH_3CH_2OH + 12CO_2$ (b) $12CO + 6H_2O \Rightarrow 3CH_3COOH + 6CO_2$ The invention will now be described in more detail with reference to the following non-limiting examples.

EXAMPLES

Media

The composition of media components used in the following examples is provided in Tables 1 and 2.

TABLE 1

Media Composition for *C. autoethanogenum*

| Media Component | Concentration per 1.0 L of Media (LM17) | Concentration per 1.0 L of Media (LM23) | Concentration per 1.0 L of Media (LM33) |
|---|---|---|---|
| $MgCl_2 \cdot 6H_2O$ | 0.5 g | 0.5 g | 0.5 g |
| NaCl | 0.2 g | 0.2 g | 0.2 g |
| $CaCl_2$ | 0.2 g | 0.2 g | 0.2 g |
| $(NH_4)_2HPO_4$ | 2.0 g | — | — |
| 100 mM sodium phosphate buffer (pH 6.0)* | — | 160 ml | — |
| $NaH_2PO_4$ | — | — | 2.04 g |
| $NH_4Cl$ | — | 0.6 g | 2.5 g |
| 85% $H_3PO_4$ | 0.05 ml | 0.05 ml | — |
| KCl | 0.15 g | 0.15 g | 0.15 g |
| Composite trace metal solution (LSO6) | 10 mL | 10 mL | 10 mL |
| Composite B vitamin Solution (LS03) | 10 mL | 10 mL | 10 mL |
| Resazurin (1000 mg/L stock) | 1 mL | 1 mL | 2 mL |
| $FeCl_3$ | 0.0025 g | 0.0025 g | 0.01 g |
| Cysteine HCl monohydrate | 0.75 g | 0.75 g | 0.5 g |
| Agarose (optional) | | 15 g | 15 g |
| Distilled water | To 1 litre | To 1 litre | To 1 litre |

*Combine $NaH_2PO_4$ (13.2 g) and $Na_2HPO_2 \cdot 7H_2O$ (1.1 g) in $H_2O$ (1 L).

TABLE 2

*C. autoethanogenum* composite mineral and vitamin solutions

| Composite B vitamin Solution (LS03) | per L of Stock | Composite trace metal solution (LSO6) | per L of stock |
|---|---|---|---|
| Biotin | 20.0 mg | Nitrilotriacetic Acid | 1.5 g |
| Folic acid | 20.0 mg | $MgSO_4 \cdot 7H_2O$ | 3.0 g |
| Pyridoxine hydrochloride | 10.0 mg | $MnSO_4 \cdot H_2O$ | 0.5 g |
| Thiamine•HCl | 50.0 mg | NaCl | 1.0 g |
| Riboflavin | 50.0 mg | $FeSO_4 \cdot 7H_2O$ | 0.1 g |
| Nicotinic acid | 50.0 mg | $Fe(SO_4)_2(NH_4)_2 \cdot 6H_2O$ | 0.8 g |
| Calcium D-(*)-pantothenate | 50.0 mg | $CoCl_2 \cdot 6H_2O$ | 0.2 g |
| Vitamin B12 | 50.0 mg | $ZnSO_4 \cdot 7H_2O$ | 0.2 g |
| p-Aminobenzoic acid | 50.0 mg | $CuCl_2 \cdot 2H_2O$ | 0.02 g |
| Thioctic acid | 50.0 mg | $AlK(SO_4)_2 \cdot 12H_2O$ | 0.02 g |
| Distilled water | To 1 Litre | $H_3BO_3$ | 0.30 g |
| | | $NaMoO_4 \cdot 2H_2O$ | 0.03 g |
| | | $Na_2SeO_3$ | 0.02 g |
| | | $NiCl_2 \cdot 6H_2O$ | 0.02 g |
| | | $Na_2WO_4 \cdot 6H_2O$ | 0.02 g |
| | | Distilled water | To 1 Litre |

LM17, LM23 and LM 33 media were prepared at pH 5.5 as follows. All ingredients with the exception of cysteine HCL were mixed in $dH_2O$ to a total volume of 1 L. This solution was made anaerobic by heating to boiling and allowing it to cool to room temperature under a constant flow of 95% CO, 5% $CO_2$ gas. Once cool, the cysteine HCL was added and the pH of the solution adjusted to 5.5; anaerobicity was maintained throughout the experiments.

Ethanol and Acetate Determinations

Ethanol and Acetate determinations in the following examples were made using a gas chromatograph HP 5890 series II-Utilizing a flame ionization detector (FID), removable, deactivated glass, injection port liner, associated regulators, gas lines, and septa with sample autoinjector HP 7673A. Separations were made on a capillary GC Column EC1000-Alltech EC1000 30 m×0.25 mm×0.25 µm.

The Gas Chromatograph was operated in Split mode with a total flow of hydrogen of 50 mL/min with 5 mL purge flow (1:10 split), a column head pressure of 20 psig resulting in a linear velocity of 45 cm/sec. The temperature program was initiated at 60° C., hold for 1 minute then ramped to 170° C. at 30° C. per minute. This resulted in a total run time of 4.65 minutes. Injector temperature was 180° C. and the detector temperature was 225° C.

Reagents used were Propan-1-ol-Reagent grade-Scharlau AL0437, Min assay by GC 99.5%; Ethanol absolute-Scharlau ET0015, Min assay by GC 99.9; Acetic acid 100% glacial-BDH 100015N, Min assay by GC 99.8%; Orthophosphoric acid-BDH 294214Q, Min assay by GC 99.0%; Nitrogen-BOC Oxygen Free-GC make up gas; Hydrogen-BOC Oxygen Free-GC carrier gas and FID fuel; Zero air-FID oxidant; Water-deionized.

Cell Density

To determine the cell density in these experiments, the absorbance of the samples was measured at 600 nm (spectrophotometer) and the dry mass determined via calculation according to published procedures. The level of metabolites was characterized using High Performance Liquid Chromatography (HPLC) and in some cases Gas Chromatography (GC).

HPLC

HPLC System Agilent 1100 Series. Mobile Phase: 0.0025N Sulphuric Acid. Flow and pressure: 0.800 mL/min. Column: Alltech IOA; Catalog #9648, 150×6.5 mm, particle size 5 μm. Temperature of column: 60° C. Detector: Refractive Index. Temperature of detector: 45° C.

The method of sample preparation for HPLC was as follows: 400 μL of sample and 50 μL of 0.15M $ZnSO_4$ and 50 μL of 0.15M $Ba(OH)_2$ are loaded into an Eppendorf tube. The tubes are centrifuged for 10 min. at 12,000 rpm, 4° C. 200 μL of the supernatant are transferred into an HPLC vial, and 5 μL are injected into the HPLC instrument.

Example 1

Production of a New Bacterial Isolate of the Invention

The new strain *Clostridium autoethanogenum* LBS1560 was produced through a dedicated program of selection and propagation of microbial cultures initiated from the parent *C. autoethanogenum* culture (DSMZ 10061) over a period of 18 months.

Methods

A frozen stock of *C. autoethanogenum* 10061 (obtained from DSMZ) was initially thawed and used to inoculate LM23 medium prepared with 5 g/litre yeast extract in the presence of 95% CO and 5% $CO_2$. This culture could not be made to grow on LM23 medium in the absence of Yeast Extract. In an effort to overcome the cultures dependence on yeast extract over a period of months, actively growing microbial cultures that were observed to produce the most ethanol and the highest ratio of ethanol to acetate were repeatedly subcultured into medium containing ever decreasing concentrations of yeast extract, always in the presence of 95% CO 5% $CO_2$ headspace gas. After this period cultures growing and producing ethanol and acetate in the absence of yeast extract could be observed. This selection protocol was actively maintained to further identify and select for cultures that:

i) grew most rapidly;
ii) produced the most ethanol;
iii) produced the highest ratio of ethanol to acetate; and,
iv) grew in the absence of yeast extract in the liquid medium.

Example 1.1

Rapid Growth Selection

In order to select for fast growing cultures, the microorganisms propensity to produce acetic acid as a by-product of energy metabolism during periods of growth on a continuous 95% CO, 5% CO2 gas stream was exploited. The accumulation of acetic acid in the growth medium has the effect of lowering the pH of the process. Accordingly, a fermenter configuration that diluted the culture in a growth dependent way in order to introduce a pressure that would select for the fastest growing populations was developed. An exemplary configuration is shown in FIG. 1, wherein a culture of microorganisms was fermented in a bioreactor 1. pH of the nutrient medium 2 was monitored by a conventional pH probe 3. Deviations in the pH reading from the set point of 5.5 caused a pump 4 to be activated, however, rather than the signal from the probe being relayed to a pump that dosed a base or acid solution; in this case the pump was linked to a bottle 5 containing fresh anaerobic LM17 media at pH 5.8. Thus as the culture grew, acetic acid was produced, the pH of the medium 2 began to drop causing the activation of a pump 4 that introduced media at pH 5.8. The pump 4 was only de-activated once the medium pH was returned to 5.5 or above. The liquid level in the reactor 1 was maintained using a level probe 6 linked to a second pump 7 that operated to maintain the liquid level in the bioreactor 1 at or below a fixed level. Medium pumped away from bioreactor 1 was passed to waste container/means 8. Accordingly, the growing culture population was diluted in a growth-linked manner and the faster the population grew, the more acetate was produced and more fresh medium was introduced until ultimately, relatively large volumes of medium were introduced into the fermenter to maintain pH effectively selecting for the fastest growing populations as these would not be washed out in an effort to maintain the liquid volume of the vessel at a fixed level. This fermenter configuration was maintained for several months at a time as a continuous culture in order to isolate fast growing cultures. Every 14 days, an aliquot of the culture was removed and allowed to grow in a 250 ml serum bottle containing 50 ml of medium and 35 psig of 95% CO, 5% CO2 in the headspace. Once actively growing the culture was prepared and stored as a glycerol stock for comparative work with the original culture stocks.

Results

The process of selection and subculture over a period of 18 months described above resulted in the new strain LBS1560 which showed optimum performance for each of features i) to iv) above. The new strain of bacteria was observed to be Gram positive (it stained Gram positive), non-motile, having a rod shape, and surprisingly exhibiting little to no ability to sporulate (as described further herein after).

LBS1560 was deposited at the DSMZ, Germany, in accordance with the Budapest Treaty, on 19 Oct. 2007, and allocated the accession number DSM 19630.

Example 2

Culture and Storage of LBS1560

*C. autoethanogenum* LBS1560 can be cultivated using the following conditions: growth on 95% CO gas (5% CO2) 35 psi in LM23 medium, at 37° C., pH 5.5, with agitation (200 rpm shaking) under anaerobic conditions. Growth may be monitored by measuring OD at 600 nm and microscopic analysis.

For storage, a log phase culture of LBS1560 in LM23+20% glycerol is flash frozen and then stored at −80° C.

Example 3

Comparison of the New *C. autoethanogenum* LBS1560 with the Original Parental Strain *C. autoethanogenum* DSMZ 10061

This experiment demonstrates the improved efficiency of the new strain LBS1560 for the anaerobic fermentation of a CO-containing gaseous substrate into ethanol, in comparison with the parental strain *C. autoethanogenum* DSMZ 10061. This experiment also demonstrates efficient fermentation of CO-containing gas to ethanol by the new strain LBS1560 in the presence of high levels CO and in the absence of $H_2$.

Methods

Frozen stocks of the selected microbial culture LBS1560, and the original parent culture DSMZ 10061 were taken, thawed and used to inoculate sealed 15 ml Hungate tubes containing 5 ml of minimal liquid anaerobic microbial growth medium (LM23) either in the presence or absence of 0.1% (w/v) yeast extract (YE). All Hungate tubes were maintained under a 95% CO, 5% $CO_2$ gas atmosphere. For each Hungate tube, microbial growth, ethanol and acetate production were monitored over a 7 day culture period.

Results

The results are presented in Table 3 below.

TABLE 3

Comparison of fermentation by strain LBS1560 and the parental strain DSMZ 10061

| Culture | Medium | Growth (g dry mass) | Ethanol (g/l) | Acetate (g/l) | Ethanol: Acetate ratio |
|---|---|---|---|---|---|
| DSMZ 10061 | LM23 + YE | 0.443 | 0.08 | 3.45 | 0.023 |
| LBS1560 | LM23 + YE | 0.0963 | 0.19 | 2.07 | 0.09 |
| DSMZ 10061 | LM23 | No growth | N/A | N/A | N/A |
| LBS1560 | LM23 | 0.583 | 2.74 | 1.95 | 1.41 |

The data presented in Table 3 highlight several reproducible differences between strain LBS1560 and the parent strain DSMZ 10061. DSMZ 10061 was unable to grow in minimal medium that lacked yeast extract, while LBS1560 could grow in medium in the presence or absence of yeast extract, but performed best on minimal medium that lacked yeast extract. LBS1560 grown on minimal medium performed better in terms of growth, ethanol production, and ethanol to acetate ratio than DSMZ 10061 grown on medium containing yeast extract.

Example 4

Sporulation Characteristics of LBS1560

To identify sporulation characteristics, LBS1560 was exposed to various conditions known to induce spore formation in bacteria in accordance with the methodology detailed below.

Starvation: a culture of LBS1560 was suspended in sterile distilled water

Exposure to Oxygen: sterile air was injected into the head space of Hungate tube containing 5 ml of growing culture, then the tube was placed on shaker and incubated at 37° C.

Exposure to Low pH Medium (pH 3): microbes were grown in LM23 (pH 5.5) to a high cell concentration, then the medium was exchanged to fresh growth medium pH 3.

Exposure to Oxygen and Fructose as Carbon and Energy Source: liquid medium contained 5 g/L of fructose and no reducing agent (i.e. cysteine-HCl) was saturated with oxygen and a high concentration of cells were suspended in this medium for 2 days.

The ability of LBS1560 to sporulate was determined by microscopic examination. Bacterial samples were stained with coomassie blue which facilitates the observation of spores. LBS1560 were observed on a number of occasions. Essentially none of the bacterial population were observed to exhibit spores. It was noted that while isolated spores were observed by microscopy in some instances, they were estimated to be significantly less than 0.1% of the overall microbial population. This was surprising and unexpected given that the parent strain and related strains of *Clostridia* are known to sporulate. The inability to sporulate provides advantages to the bacteria of the invention as herein before described.

Example 5

Ethanol Production by LBS1560

Figure 1:
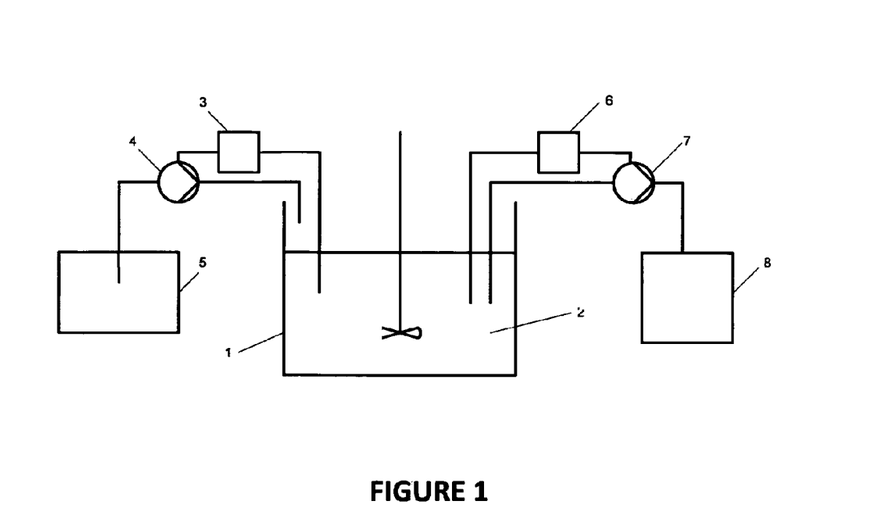
FIG. 1: is a schematic representation of a system adapted to select for rapid microbial growth
Figure 2:
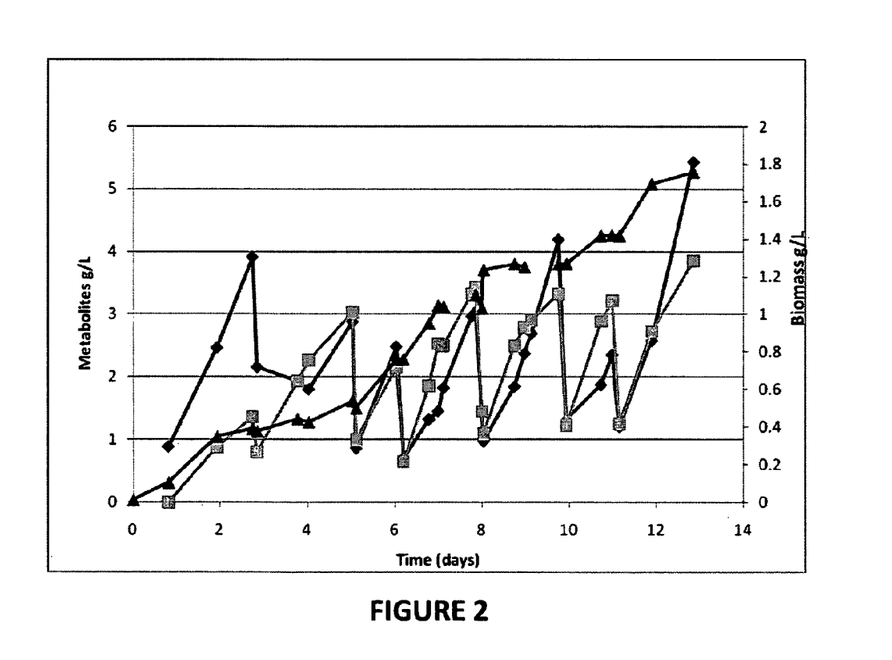
FIG. 2: shows ethanol (square) and acetate (diamond) production by Clostridium autoethanogenum LBS1560. Biomass concentration is represented by the triangle data points.

This example describes continuous ethanol production by LBS1560 over an extended period. FIG. 2 provides a summary of the concentrations of acetate, ethanol and biomass over a 2 week period.

Procedure 1. 1 L medium of anaerobic LM33 fermentation media in a 1 Litre CSTR was inoculated with an actively growing *Clostridium autoethanogenum* (LBS1560) culture (DSMZ 19630) at a level of 5% (v/v). A continuous flow of 70% CO and 15% $CO_2$ 1% $H_2$ 14% $N_2$ gas was introduced at the bottom of the fermenter vessel through a diffusing sparger at a volumetric flow rate of 19 ml/minutes. The initial pH of the fermenter was set to 5.5 and the agitation speed was adjusted to 400 rpm.

2. For the majority of the experiment, the acetic acid concentration of the culture was maintained below 4 g/L by a cell recycle and media exchange system. The cells were passed through a cross flow membrane Viva 200, the filtrate was collected and the cells were returned to the reactor vessel. The filtrate was replaced with fresh medium to ensure the medium volume inside the reactor remained constant.

3. The culture was operated continuously for at least 14 days. The cell recycle system removed 1-1.5 L of liquid nutrient medium every 1-2 days without removing bacteria from the bioreactor. The removed medium was replaced with fresh media, to maintain constant volume.

4. The pH of the fermenter was increased from 5.6 to 6.0 over the first four days of the experiment.

Results

The rapid growth phase of acetogenic bacteria (such as *C. autoethanogenum*) is typically associated with high acetate production in a controlled fermentation environment. In this experiment, using the novel strain LBS1560, during the growth phase (day 0-3) the culture produced an average of 0.3 g/L/day acetate and 0.16 g/L/day ethanol. Following the growth phase (day 3-13) the culture produced an average of 1.03 g/L/day acetate and an average of 1.4 g/L/day ethanol. Over the alcohol production period total ethanol produced was 14 g/L. The results show a lower than expected level of acetate production and significantly higher ethanol production.

The specific methods and compositions described herein are representative of preferred embodiments and are exemplary and not intended as limitations on the scope of the invention. Other objects, aspects and embodiments will occur to those skilled in the art upon consideration of this specification, and are encompassed within the scope and spirit of the invention. It will be readily apparent to one skilled in the art that varying substitutions and modifications may be made to the invention disclosed herein without departing from the scope and spirit of the invention. The invention illustratively described herein suitably may be practised in the absence of any element or elements, or limitation or limitations, which is not specifically disclosed herein as essential. Thus, for example, in each instance herein, in embodiments or examples of the present invention, the terms "comprising", "including", "containing" etc are to be read expansively and without limitation. Furthermore, titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

The invention claimed is:

1. A biologically pure isolate of a bacterium derived from *Clostridium autoethanogenum*, the bacterium having the defining characteristics of the *Clostridium autoethanogenum* strain deposited at the German Collection of Microorganisms and Cell Cultures (DSMZ) under the accession number DSM 19630, said bacterium characterised by the ability to produce products comprising ethanol and acetate, by anaerobic fermentation of a substrate comprising CO.

2. The biologically pure isolate of claim 1, wherein the ethanol to acetate ratio is at least 1.0.

3. The biologically pure isolate of claim 1, wherein the bacterium has an ethanol productivity of at least about 1.2 g of ethanol/L of fermentation broth/day.

4. The biologically pure isolate of a bacterium as claimed in of claim 1, wherein the substrate is greater than 65% CO by volume.

5. The biologically pure isolate of claim 1, wherein the bacterium is the *Clostridium autoethanogenum* strain deposited at DSMZ under the accession number 19630.

6. The biologically pure isolate of claim 1, wherein the ethanol to acetate ratio is at least 1.2.

7. The biologically pure isolate of claim 1, wherein the bacterium has an ethanol productivity of at least about 2.0 g of ethanol/L of fermentation broth/day.

* * * * *